(12) United States Patent
Algawi et al.

(10) Patent No.: US 11,707,341 B2
(45) Date of Patent: Jul. 25, 2023

(54) JIG FOR ASSEMBLING A POSITION SENSOR

(71) Applicant: BIOSENSE WEBSTER (ISRAEL) LTD, Yokneam (IL)

(72) Inventors: Yehuda Algawi, Binyamina (IL); Assaf Govari, Haifa (IL); Ilya Sitnitsky, Nahariya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 505 days.

(21) Appl. No.: 16/806,259

(22) Filed: Mar. 2, 2020

(65) Prior Publication Data
US 2021/0267712 A1 Sep. 2, 2021

(51) Int. Cl.
| | |
|---|---|
| *B23P 19/00* | (2006.01) |
| *H05K 13/04* | (2006.01) |
| *A61B 90/50* | (2016.01) |
| *A61B 34/20* | (2016.01) |
| *A61B 5/06* | (2006.01) |
| *H05K 3/00* | (2006.01) |
| *G01R 33/00* | (2006.01) |

(52) U.S. Cl.
CPC ............. *A61B 90/50* (2016.02); *A61B 34/20* (2016.02); *A61B 5/062* (2013.01); *A61B 2562/12* (2013.01); *A61B 2562/164* (2013.01); *G01R 33/0052* (2013.01); *H05K 3/00* (2013.01); *H05K 2203/00* (2013.01)

(58) Field of Classification Search
CPC ...... H05K 1/028; H05K 1/189; H05K 3/0061; H05K 2203/00; H05K 2201/086; H05K 2201/10151; B23P 19/00; A61B 90/50; A61B 34/20; A61B 2562/12; A61B 2562/164; A61B 2562/166; A61B 5/062; B21D 5/16; G01R 33/0052
See application file for complete search history.

(56) References Cited

U.S. PATENT DOCUMENTS

| | | | |
|---|---|---|---|
| 5,391,199 A | 2/1995 | Ben-Haim | |
| 5,434,362 A | 7/1995 | Klosowiak et al. | |
| 6,239,724 B1 | 5/2001 | Doron et al. | |
| 6,332,089 B1 | 12/2001 | Acker et al. | |
| 6,484,118 B1 | 11/2002 | Govari | |
| 6,501,661 B1 * | 12/2002 | Moore ................... | H05K 1/189 361/752 |
| 6,618,612 B1 | 9/2003 | Acker et al. | |
| 6,690,963 B2 | 2/2004 | Ben-Haim et al. | |

(Continued)

FOREIGN PATENT DOCUMENTS

| | | |
|---|---|---|
| WO | WO 95/09562 | 4/1995 |
| WO | WO9605768 | 2/1996 |

OTHER PUBLICATIONS

International Search Report dated May 25, 2021 from corresponding PCT Patent Application No. PCT/IB2021/051534.

*Primary Examiner* — Paul D Kim
(74) *Attorney, Agent, or Firm* — Frost Brown Todd LLP (57) ABSTRACT

A jig includes a base and one or more movable blocks. The base has an upper surface, which is configured to receive a substrate shaped as a flattened polyhedron having multiple facets. The one or more movable blocks are configured to move on the base so as to fold respective ones of the multiple facets, and to hold the substrate in a folded three-dimensional configuration.

20 Claims, 4 Drawing Sheets

(56) References Cited

U.S. PATENT DOCUMENTS

| | | | |
|---|---|---|---|
| 7,040,922 B2* | 5/2006 | Harney | B81B 7/0074 |
| | | | 361/810 |
| 9,119,317 B2* | 8/2015 | Primavera | H05K 7/16 |
| 9,243,909 B2* | 1/2016 | Sakuma | G01P 1/026 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2011/0067232 A1 | 3/2011 | Conger et al. | |
| 2013/0111993 A1 | 5/2013 | Wang | |
| 2014/0090243 A1 | 4/2014 | Primavera | |
| 2014/0160692 A1 | 6/2014 | Lau | |
| 2014/0254114 A1 | 9/2014 | Hattori et al. | |
| 2018/0238930 A1 | 8/2018 | Nguyen et al. | |

* cited by examiner

JIG FOR ASSEMBLING A POSITION SENSOR

FIELD OF THE INVENTION

The present invention relates generally to assembly tools, and particularly to methods and systems for assembling a position sensor.

BACKGROUND OF THE INVENTION

Some electronic devices comprise foldable substrates that are assembled using various techniques.

For example, U.S. Patent application publication 2014/0090243, issued as U.S. Pat. No. 9,119,317 on Aug. 25, 2015, describes a method for manufacturing devices built on flexible substrates employs an in-situ, fold-assisting device frame. The fold-assisting frame conforms to a portion of the interior volume within the package, such that one or more pivoting members of the frame may be used as an in-situ, bending jig, in place of conventional bending equipment, to support and fold the planar flexible substrate into a desired three-dimensional configuration. The frame may accommodate placement of an unfolded or partially folded flexible circuit board so that a fold-assisting feature, such as a hinge, incorporated into the frame attaches to the flexible circuit board and closes around a pivot point to gently bend the circuit board into place, thus creating a three-dimensional folded circuit.

U.S. Pat. No. 5,434,362 describes a flexible circuit board assembly including a flexible substrate having first and second end portions, and an intermediate portion. Conductive metalization interconnect paths extend between the substrate end portions and across the intermediate portion. The substrate first and second end portions are mounted to first and second end portions of a rigidizer plate.

SUMMARY OF THE INVENTION

An embodiment of the present invention that is described herein provides a jig including a base and one or more movable blocks. The base has an upper surface, which is configured to receive a substrate shaped as a flattened polyhedron having multiple facets. The one or more movable blocks are configured to move on the base so as to fold respective ones of the multiple facets, and to hold the substrate in a folded three-dimensional configuration.

In some embodiments, the base includes at least a track for moving at least one of the movable blocks. In other embodiments, the substrate includes a foldable section between adjacent facets, and at least one of the movable blocks is configured to fold the foldable section and to fasten one of the adjacent facets to a respective solid facet of a solid polyhedron. In yet other embodiments, the jig includes at least a fixation apparatus, which is configured to fixate at least one of the movable blocks at a predefined position on the base.

In an embodiment, the jig includes a knob, which is fixated to the base and is configured to fasten at least one of the facets to a respective solid facet of a solid polyhedron. In another embodiment, the jig includes a mechanical supporting part, which is configured to be fixated to the base and has a bore, the knob is configured to pass through the bore, such that a distal end of the knob is configured to be moved toward the solid polyhedron for fastening the at least one of the facets to the respective solid facet. In yet another embodiment, the mechanical supporting part includes a bridge that goes over the solid polyhedron, and, when the bridge is fixated to the base, the bore is aligned with the respective solid facet.

In some embodiments, the knob includes a screw, and the bore includes a screw-shaped bore configured to snugly fit over the screw. In other embodiments, the knob is configured to be rotated in first and second directions that are opposite to one another, when the knob is rotated in the first direction, the distal end is configured to move toward the solid polyhedron, and when the knob is rotated in the second direction, the distal end is configured to move away from the solid polyhedron. In yet other embodiments, the substrate includes an upper facet, a lower facet and one or more additional facets, a solid polyhedron is positioned on the lower facet, the one or more movable blocks are configured to fasten respective ones of the additional facets to respective solid facets of the solid polyhedron, and the jig includes a knob, which is configured to fasten the upper facet to an upper solid facet of the solid polyhedron.

There is additionally provided, in accordance with an embodiment of the present invention, an assembling method including placing, on an upper surface of a base, a substrate shaped as a flattened polyhedron having multiple facets. A solid polyhedron is positioned on at least one of the facets. One or more movable blocks are moved on the base for folding respective ones of the multiple facets onto respective solid facets of the solid polyhedron, and the substrate is held in a folded three-dimensional configuration against the solid polyhedron.

In some embodiments, the method includes coupling, to one another, adjacent edges of the folded facets for wrapping the polyhedron with the substrate. In other embodiments, coupling the adjacent edges includes using a coupling technique selected from a list consisting of: (a) welding, (b) soldering, (c) gluing, (d) stapling, and (e) clipping.

The present invention will be more fully understood from the following detailed description of the embodiments thereof, taken together with the drawings in which:

DETAILED DESCRIPTION OF EMBODIMENTS

Overview

Embodiments of the present invention that are described hereinbelow provide methods and apparatus for improving the manufacturability of position sensors used in a magnetic position tracking system for medical applications.

In some embodiments, a triple-axis position sensor (TAPS) comprises a ferrite cube, also referred to herein as a solid cube or a cube, wrapped with a foldable substrate, such as a flexible printed circuit board (PCB), having multiple foldable facets. Wrapping the solid cube with the PCB involves folding the PCB facets onto respective facets of the solid cube and coupling between the edges of the PCT facets for fastening the PCB facets to the facets of the solid cube. Such a complex and time-consuming operation may be carried out manually (e.g., by an operator), or using one or more robots.

In some embodiments, a jig is provided for assembling the TAPS. The jig comprises a base having an upper surface and four tracks patterned in the base. The base is configured to receive the PCB shaped as a flattened cube having six facets, also referred to herein as first to sixth ($1^{st}$-$6^{th}$) facets. During the assembly process, the cube is placed on the first facet of the PCB.

In some embodiments, the jig comprises four movable blocks, which are configured to move along the respective four tracks of the base, so as to fold the second, third, fourth and fifth facets of the PCB onto four solid facets of the cube, respectively. The base and each block have bores, and the jig comprises four pins for fixating the four respective blocks at predefined positions on the base, so as to hold the PCB in a folded three-dimensional configuration against the solid facets of the cube.

In some embodiments, the jig comprises a fastener having a bridge fixed to the base, and a knob configured to move through a bore of the bridge for fastening the sixth PCB facet to the cube.

In some embodiments, when the blocks and fastener are fixated to the base, the jig is configured to fasten all the PCB facets to the respective cube facets. In such embodiments, the operator hands are free for coupling (e.g., welding, soldering or gluing) edges of adjacent PCB facets, so as to complete wrapping of the cube by the PCB.

The disclosed techniques improve the assembling quality and reduce the production costs of devices or components wrapped with foldable substrates.

System Description

Figure 1:
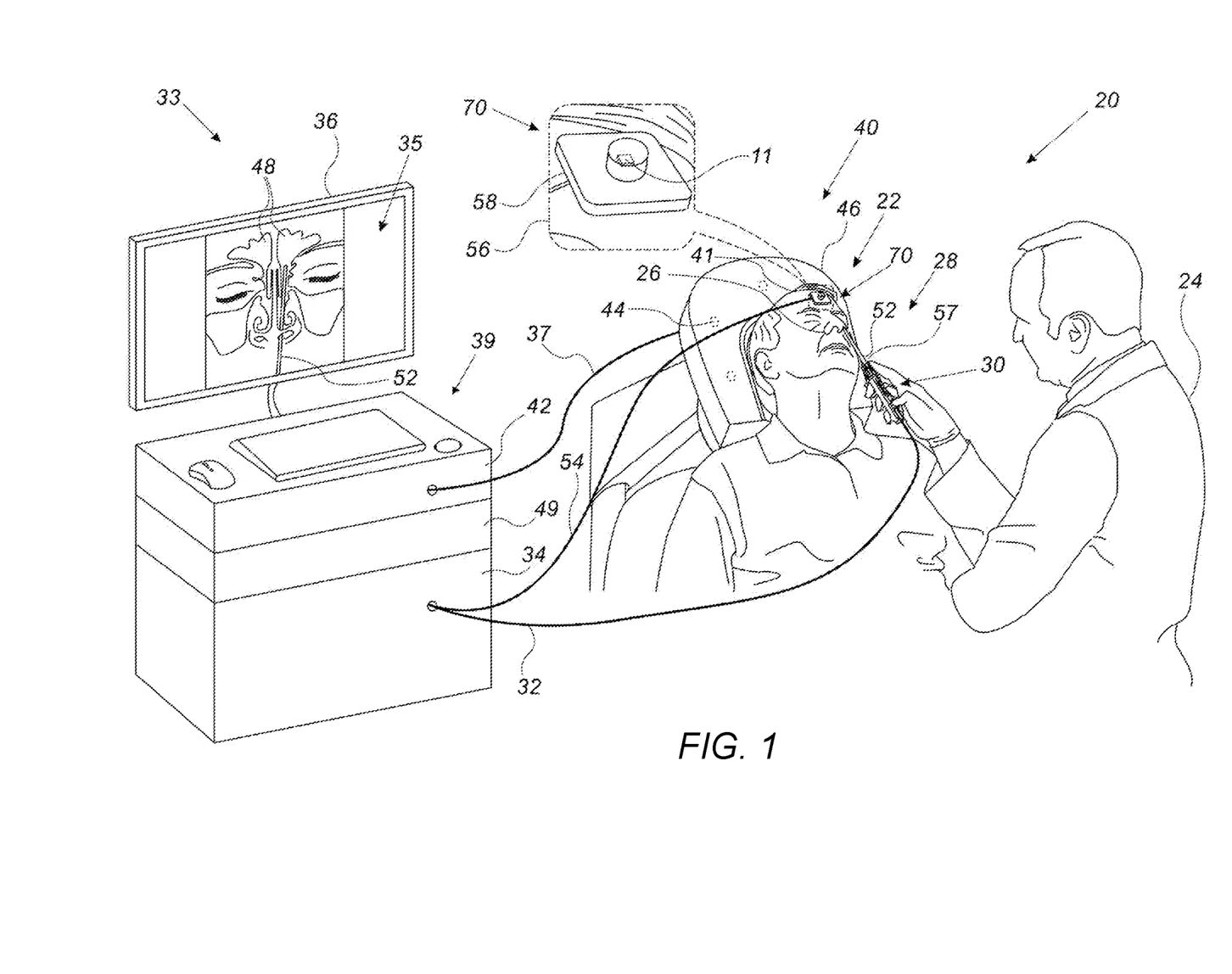
FIG. 1 is a schematic, pictorial illustration of an ear-nose-throat (ENT) procedure using an ENT system, in accordance with an embodiment of the present invention.

FIG. 1 is a schematic, pictorial illustration of an ear-nose-throat (ENT) procedure using an ENT system 20, in accordance with an embodiment of the present invention. In some embodiments, the ENT procedure may comprise a balloon sinuplasty procedure in which a balloon (not shown) is inserted into a blocked ostium of a sinus 48, and is inflated so as to open the ostium for enabling a regular flow and evacuation of mucus from the sinus through a nasal cavity of a nose 26 of a patient 22. In other embodiments, the ENT procedure may comprise any other diagnostic or treatment procedure carried out in the patient ENT. In such embodiments, ENT system 20 comprises a medical catheter, in the present example an ENT tool 28, which is configured to carry out one or more of the ENT procedures in one or more sinuses 48 of patient 22.

In some embodiments, ENT tool 28 comprises a rotatable hollow tube, referred to herein as a tube 52, which is inserted, by a physician 24, into a cavity, such as the aforementioned nasal cavity of nose 26, of patient 22. ENT tool 28 further comprises a handheld apparatus 30, coupled to a proximal end of tube 52 and configured to assist physician 24 to carry out the ENT procedure in a head 41 of patient 22.

In an embodiment, system 20 further comprises a magnetic position tracking system, which is configured to track the position of one or more position sensors in head 41. The magnetic position tracking system comprises magnetic field-generators 44 and a position sensor 57, which generates position signals in response to sensing external magnetic fields generated by field-generators 44, thereby enabling a processor 34 (described in detail below) to estimate the position of position sensor 57 within head 41 of patient 22.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004; 2003/0120150 A1, issued as U.S. Pat. No. 7,729,742 on Jun. 1, 2010; and 2004/0068178 A1, now abandoned, whose disclosures are all incorporated herein by reference.

In some embodiments, system 20 further comprises a location pad 40, which comprises field-generators 44 fixed on a frame 46. In the exemplary configuration shown in FIG. 1, pad 40 comprises five field-generators 44, but may alternatively comprise any other suitable number of field-generators 44. Pad 40 further comprises a pillow (not shown) placed under head 41 of patient 22, such that field-generators 44 are located at fixed and known positions external to head 41.

In some embodiments, system 20 comprises a console 33, which comprises a memory 49, and a driver circuit 42 configured to drive, via a cable 37, field-generators 44 with suitable signals so as to generate magnetic fields in a predefined working volume in space around head 41.

In some embodiments, console 33 comprises processor 34, typically a general-purpose computer, with suitable front end and interface circuits for receiving signals from ENT tool 28 having one or more magnetic sensors 57 coupled thereto, via a cable 32, and for controlling other components of system 20 described herein.

In some embodiments, processor 34 is configured to estimate the position of each position sensor 57. Based on the estimated positions of the respective sensors, in the coordinate system of the magnetic position tracking system, processor 34 is configured to derive the position, orientation and radius of curvature of distal-end assembly 77.

In the context of the present invention, the terms "bending" "deflecting" are used interchangeably and refer to steering of one or more sections of ENT tool 28.

In some embodiments, processor 34 is configured to receive via an interface (not shown), one or more anatomical images, such as computerized tomography (CT) images depicting respective segmented two-dimensional (2D) slices of head 41, obtained using an external CT system (not shown). The term "segmented" refers to displaying various types of tissues identified in each slice by measuring respective attenuation of the tissues in the CT system.

Console 33 further comprises input devices 39 for controlling the operation of system 20, and a user display 36, which is configured to display the data (e.g., images) received from processor 34 and/or to display inputs inserted by physician 24 or another user of input devices 39.

In some embodiments, processor 34 is configured to select one or mode slices from among the CT images, such as an anatomical image 35, and to display the selected slice on user display 36. In the example of FIG. 1, anatomical image 35 depicts a sectional front-view of one or more sinuses 48 of patient 22.

In some embodiments, processor 34 is configured to register between the coordinate systems of the CT system and the magnetic position tracking system, and to overlay the position of distal-end assembly 77, on anatomical image 35.

In some cases, head 41 of patient 22 may undesirably be moved during the ENT procedure. The undesired move may result in a misregistration between the coordinate systems of the CT system and the magnetic position tracking system. In some embodiments, system 20 comprises a position tracking assembly (PTA) 70, which is coupled to the forehead of patient 22 or to any suitable position of head 41.

Reference is now made to an inset 56 showing PTA 70. In some embodiments, PTA 70 comprises a triple axis position sensor (TAPS) 11, which is coupled to console 33 via a cable 54, and is configured to generate position signals in response to sensing the external magnetic fields produced by field-generators 44.

In some embodiments, processor 34 is configured to register TAPS 11 in the coordinate system of the position tracking system (e.g., before the ENT procedure). Note that head 41 is considered a rigid object, therefore, when ENT tool 28 is positioned at head 41 without moving, the distance between position sensor 57 and TAPS 11 remains constant.

In some embodiments, in response to the aforementioned undesired move of head 41, processor 34 is configured to use the position signals of TAPS 11 for correcting the misregistration described above. In such embodiments, based on the position signals received from TAPS 11, processor 34 is configured to estimate the shift of TAPS 11 caused by the undesired move of head 41, and to compensate for the shifting by adding an offset (e.g., a vector) to the measured position of position sensor 57.

In the example configuration of inset 56, TAPS 11 is mounted on a substrate 58, which is configured to be coupled to the forehead of patient 22. In other embodiments, TAPS 11 may be coupled to head 41 using any suitable coupling technique. TAPS 11 and an assembly process thereof are described in more details in FIGS. 2-5 below.

System 20 typically comprises additional modules and elements that are not directly related to the disclosed techniques, and therefore, are intentionally omitted from FIG. 1 and from the description of system 20.

Processor 34 may be programmed in software to carry out the functions that are used by the system, and to store data in memory 49 to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of medical diagnostics and/or treatment tools and/or systems.

A Jig for Assembling a Triple Axis Position Sensor

Figure 2:
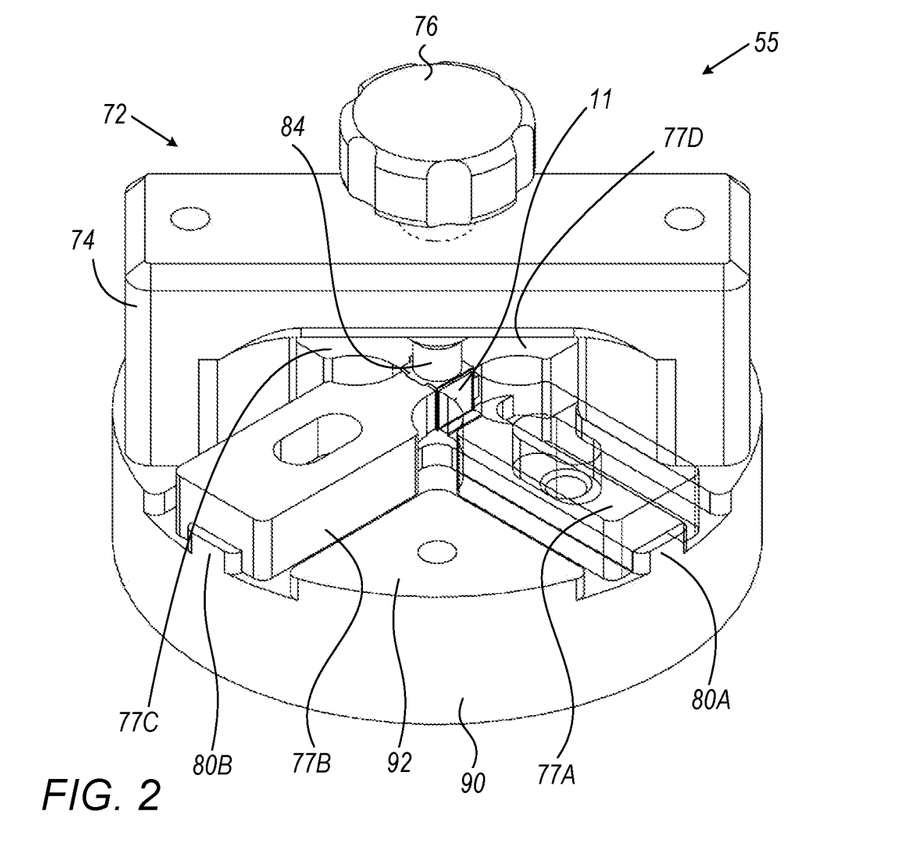
FIG. 2 is a schematic, pictorial illustration of a jig for assembling a triple axis position sensor (TAPS), in accordance with an embodiment of the present invention.

FIG. 2 is a schematic, pictorial illustration of a jig 55 for assembling triple axis position sensor (TAPS) 11, in accordance with an embodiment of the present invention. In some embodiments, TAPS 11 comprises a polyhedron typically made from or comprising ferrite or any other suitable materials, or one or more alloys.

In the present example, TAPS 11 comprises a ferrite cube (shown in FIG. 4 below), which is surrounded by (e.g., wrapped-around with) a flexible printed circuit board (PCB) (shown in FIG. 3 below) having conductive traces for enabling the triple-axis position-sensing capabilities of TAS 11.

In some embodiments, jig 55 has a base 90 having an upper surface 92 and four tracks, such as tracks 80A and 80B, formed (e.g., patterned) in base 90. The tracks are shown and described in more detail in FIG. 4 below. Base 90 is configured to receive a substrate, such as the aforementioned PCB, which is shaped as a flattened polyhedron having multiple facets. In the present example, TAPS 11 comprises a cube, so that the substrate is shaped as a flat cube having six facets.

In some embodiments, jig 55 comprises four blocks 77A, 77B, 77C and 77D, which are configured to move along the aforementioned tracks on upper surface 92 of base 90, so as to fold respective ones of the cube facets. For example, blocks 77A and 77B are moving along tracks 80A and 80B, respectively. In the example of FIG. 2, block 77A is shown as a transparent element, so as to show TAPS 11 for the sake of conceptual clarity. In other embodiments, block 77A, which is moved along track 80A, has the same shape, color and opacity of blocks 77B, 77C and 77D.

In some embodiments, when coupled to the ferrite cube (as shown in FIG. 2), blocks 77A, 77B, 77C and 77D are configured to hold the facets of the substrate in a folded three-dimensional configuration against respective solid facets of the ferrite cube. Moreover, when fixated at predefined positions on base 90, blocks 77A, 77B, 77C and 77D are configured to fasten four facets of the substrate to respective solid facets of the ferrite cube.

In the concept of the present invention and in the claims, the terms "substrate" and "PCB" are used interchangeably. Moreover, the terms "polyhedron" and "cube" that is a specific type of the polyhedron, are used interchangeably. Note that in the example of FIGS. 2-4, TAPS 11 is shaped as a cube, however, the embodiments described herein may be applied, mutatis mutandis, for assembling any type of polyhedron. For example, TAPS 11 may be shaped as a pentagon, a hexagon, an octagon or any other suitable shape.

In other embodiments, TAPS 11 may have any suitable shape, other than polyhedron, such as but not limited to, a ball of an ellipse.

In some embodiments, jig 55 comprises a fastener 72, which is configured to fasten a facet of the substrate to an upper solid facet (shown in FIG. 4 below) of the ferrite cube of TAPS 11. In some embodiments, fastener 72 comprises a mechanical supporting part, referred to herein as a bridge 74, which is fixed to upper surface 92 at two locations. Bridge 74 is configured to provide a mechanical support to a knob 76 passing therethrough as described herein. In some embodiments, knob 76 is configured to fasten at least one of the facets of the substrate to a respective solid facet of a solid cube of TAPS 11.

In an embodiment, knob 76 is shaped as a screw (not shown) and bridge 74 has a corresponding screw-shaped bore configured to snugly fit over the screw. In this embodiment, when knob 76 is being rotated (e.g., clockwise) a distal end 84 of knob 76 is pushed toward the upper facet of TAPS 11 and is configured to fasten the respective facet of the substrate to the upper facet of the cube.

In some embodiments, after having all facets of the substrate fastened to the respective solid facets of the cube, the edges of adjacent facets of the substrate may be coupled to one another (e.g., using welding, soldering, gluing, or any other suitable technique) so as complete the assembly of TAPS 11. The assembly process is described in more detail in FIG. 5 below.

This particular configuration of jig 55 is shown by way of example, in order to illustrate certain problems that are addressed by embodiments of the present invention and to demonstrate the application of these embodiments in enhancing the performance of such a jig for assembling TAPS 11 and other types of devices. Embodiments of the present invention, however, are by no means limited to this specific sort of example jig, and the principles described herein may similarly be applied to other sorts of jigs and devices to be assembled.

For example, in case TAPS 11 is shaped as a volumetric hexagon having a lower facet, an upper facet, and six additional facets, jig 55 may have six tracks and six respective blocks for holding, respectively, six facets of the substrate against the six additional facets of the volumetric hexagon. In another example, in case TAPS 11 is shaped as a ball, the edge (that touching the ball) of at least one of the blocks, may be shaped as an arc, so as to snugly-fit over the ball for holding a section of the substrate against the surface of the ball.

Substrate for Assembling the Triple Axis Position Sensor

Figure 3:
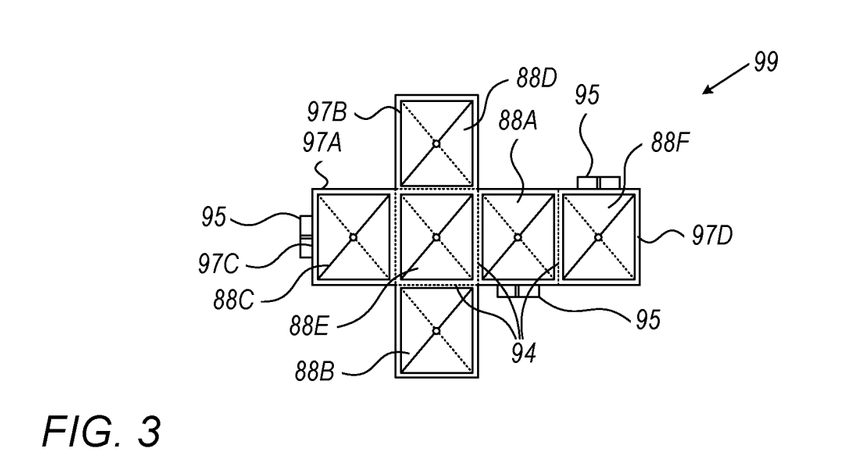
FIG. 3 is a schematic, pictorial illustration of a foldable substrate of a TAPS, in accordance with an embodiment of the present invention.

FIG. 3 is a schematic, pictorial illustration of a foldable substrate used for assembling TAPS 11, in accordance with an embodiment of the present invention. In the present example, the foldable substrate comprises a printed circuit board (PCB) 99 having multiple foldable sections, such as sections 94, laid out between six facets 88A, 88B, 88C, 88D, 88E and 88F corresponding to the six solid facets of the aforementioned solid cube (shown in FIG. 4 below) of TAPS 11.

In some embodiments, facets 88A-88F may be flexible or rigid, however, sections 94 are flexible so as to enable the folding of facets 88A-88F around the cube of TAPS 11. Note that facet 88E, which is intended to be fastened to the lower solid facet of the cube of TAPS 11, is surrounded by four sections 94.

In some embodiments, facets 88A-88F have edges configured to be coupled to one another. For example, facets 88C and 88D are coupled to one another by coupling between an edge 97A of facet 88C and an edge 97B of facet 88D. Similarly, facets 88C and 88F are coupled to one another by coupling between an edge 97C of facet 88C and an edge 97D of facet 88F. As described above, after having all facets 88A-88F fastened to the respective solid facets of the cube, the edges of adjacent facets (e.g., edges 97A and 97B of respective facets 88C and 88D) of PCB 99, may be coupled to one another so as complete the assembly of TAPS 11.

In some embodiments, the coupling between adjacent edges may be carried out using one or more coupling techniques, such as but not limited to welding, micro-welding, soldering, gluing, stapling, clipping, or any other suitable technique. In some embodiments, one or more facets of PCB 99 may have a band for the coupling process. In the example of FIG. 3, facets 88A, 88C and 88F have bands 95 configured for gluing adjacent facets of PCB 99 to one another. The assembly process is described in more detail in FIG. 5 below.

Figure 4:
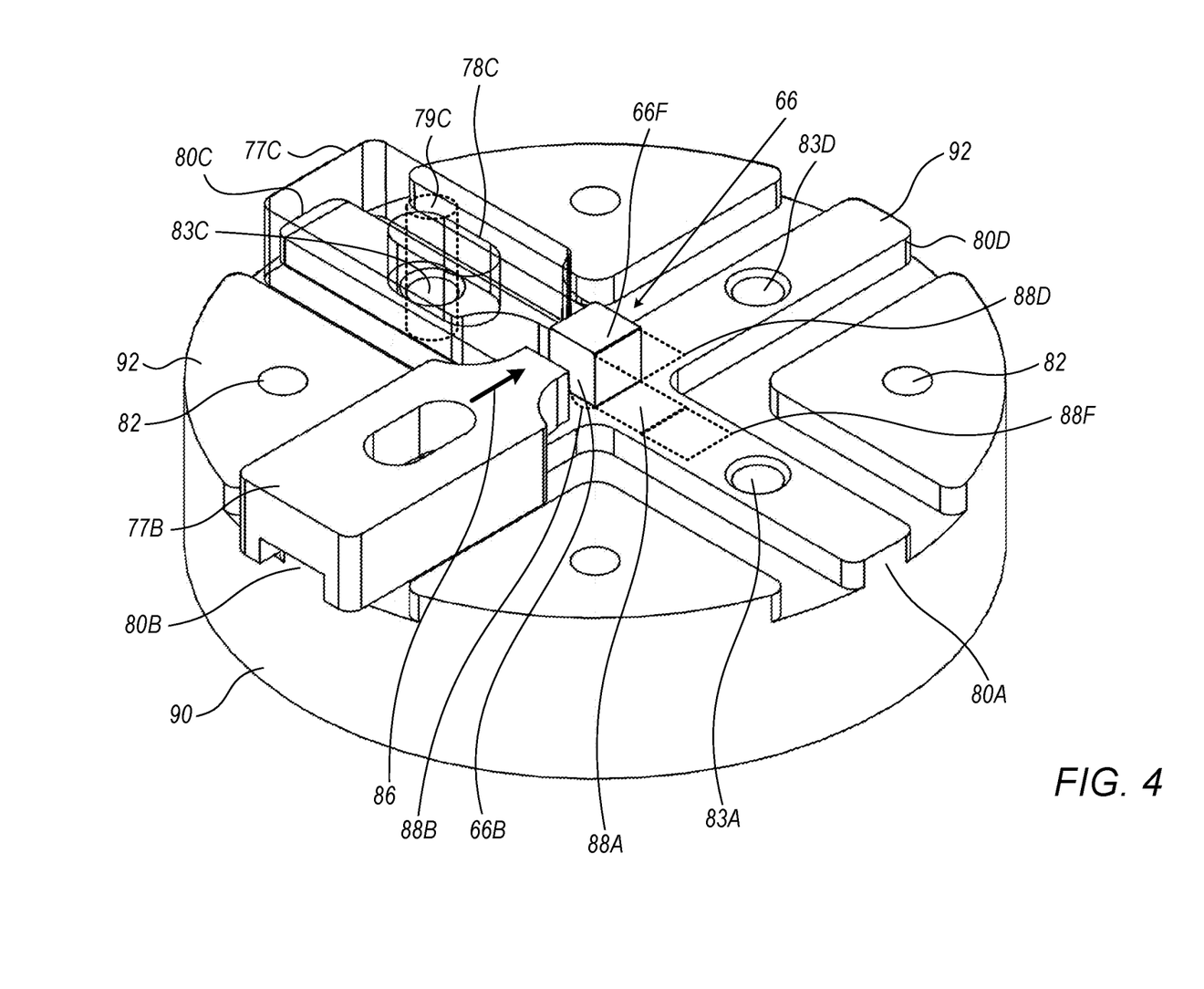
FIG. 4 is a schematic, pictorial illustration of a base and blocks of a jig for assembling a TAPS, in accordance with an embodiment of the present invention.

Mechanical Structure of the Base of the Jig for Assembling the Triple Axis Position Sensor FIG. 4 is a schematic, pictorial illustration of base 90 and blocks 77B and 77C of jig 77, in accordance with an embodiment of the present invention. In some embodiments, base 90 has tracks 80A, 80B, 80C and 80D configured for setting the corresponding moving directions of blocks 77A, 77B, 77C and 77D, respectively.

In some embodiments, base 90 has bores 82 configured for fixating bridge 74 to upper surface 92 of base 90, and similarly, bridge 74 has two corresponding bores (not shown) configured for the fixation. In such embodiments, a pin (not shown) may be inserted into each bore 82, and the corresponding bores of bridge 74 may be fitted over the pins so as to fixate bridge 74 to upper surface 92 of base 90.

In some embodiments, during the assembly process of TAPS 11, PCB 99 is placed on upper surface 92, such that facet 88E is positioned at the center of base 90, facets 88A, 88B, 88C and 88D, are placed on tracks 80A, 80B, 80C and 80D, respectively, and facet 88F that is coupled to facet 88A, is also placed on track 80A.

In some embodiments, after positioning PCB 99 on surface 92, a cube 66 made from or comprising ferrite, is positioned on facet 88E (hidden by cube 66). Subsequently, blocks 77A-77D are moved along tracks 80A-80D, so as to fold the respective facets of PCB 99, and to hold PCB 99 in a folded three-dimensional configuration against the respective facets of cube 66. In the example of FIG. 4, block 77C is already moved along track 80C of base 90 and reaches cube 66, so as to fold and hold facet 88A against a corresponding solid facet of cube 66.

In some embodiments, block 77B is being moved along track 80B in a direction 86, for the sake of folding and holding facet 88B against a solid facet 66B of cube 66. As shown in FIG. 4, facet 88B is being folded by the move of block 77B, but is not yet fastened to solid facet 66B because block 77B has not yet reached solid facet 66B.

In some embodiments, base 90 has bores, such as bores 83A, 83C and 83D, for fixating the position of the respective blocks (e.g., blocks 77A, 77C and 77D) to upper surface 92 of base 90. Note that base 90 has an additional bore for fixating block 77B to upper surface 92 of base 90. In the example of FIG. 4, the additional bore is hidden by block 77B.

In some embodiments, at least one of blocks 77A-77D has a bore for fixating the respective block to upper surface 92 of base 90. In the present configuration, all blocks 77A-77D have respective bores, for example, block 77C (shown as a transparent block for the sake of description and conceptual clarity) has a bore 78C. In the example of FIG. 4, when block 77C is holding facet 88C against the corresponding solid facet of cube 66, bore 78C (of block 77C) and bore 83C (of base 90) are aligned.

In some embodiments, a robot or an operator (neither shown) of jig 55, may insert a pin 79C (shown in dashed line for the sake of description and conceptual clarity) through bores 78C and 83C, so as to fixate block 77C on upper surface 92, and therefore, to fasten facet 88C to the solid facet of cube 66. In case of a manual fixation, after inserting pin 79C through bores 78C and 83C, block 77C is fixated to upper surface 92, and the operator hands are free for inserting and moving block 77B in direction 86. In such embodiments, by moving block 77B along track 80B in direction 86, jig 55 folds facet 88B (shown as a dashed arc), and when block 77B reaches the position of cube 66, facet 88B is fastened to solid facet 66B of cube 66.

In the context of the present disclosure and in the claims, the terms "fastened to" and "holding against" are used interchangeably and are used for describing how jig 55 is used for coupling between a facet of PCB 99 and a corresponding facet of cube 66.

In some embodiments, blocks 77A and 77D (shown in FIG. 2 above) are configured to move along respective tracks 80A and 80D, so that facets 88A and 88D are fastened to the respective solid facets of cube 66, using the techniques described for facets 77B and 77C. As described above, cube 66 is positioned on facet 88E so that facets 88A-88D are fastened to the corresponding facets of cube 66. Subsequently, the operator (or robot) may fold facet 88F on a solid facet 66F of cube 66, and rotates knob 76 (e.g., clockwise) to move distal end 84 toward cube 66 for fastening facet 88F to solid facet 66F.

After having all facets 88A-88F held in a folded three-dimensional configuration and fastened to the respective solid facets of cube 66, the operator (or a robot) may complete the assembling process by coupling the edges of adjacent facets to one another. For example, by coupling between edges 97A and 97B of respective facets 88C and 88D, as described above.

Assembling Process of the Triple Axis Position Sensor

Figure 5:
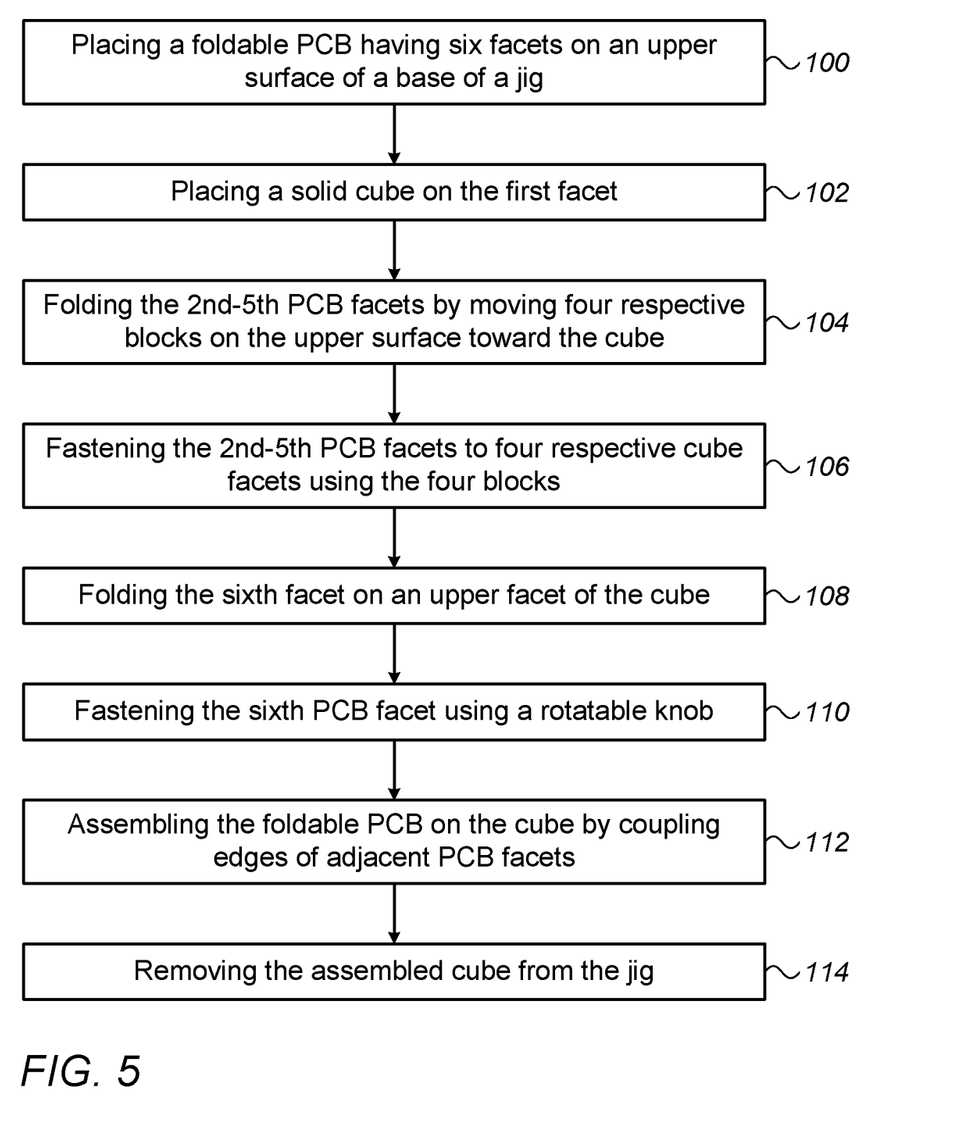
FIG. 5 is a flow chart that schematically illustrates a method for producing a TAPS using the jig of FIG. 2, in accordance with an embodiment of the present invention.

FIG. 5 is a flow chart that schematically illustrates a method for producing TAPS 11 using jig 55, in accordance with an embodiment of the present invention. The method begins at a substrate placing step 100 with placing PCB 99, or any other suitable foldable substrate, having six facets (e.g., facets 88A-88F) on upper surface 92 of base 90 of jig 55.

At a cube placing step 102, cube 66, or any other suitable type of a solid polyhedron, is placed on facet 88E (also referred to herein as a first facet of PCB 99), as described in FIG. 4 above. At a first folding step 104, facets 88A, 88B, 88C and 88D (also referred to herein as second, third, fourth and fifth facets of PCB 99) are folded by moving four respective blocks 77A, 77B, 77C and 77D on upper surface 92 toward cube 66. At a first fastening step 106, facets 88A, 88B, 88C and 88D are fastened to (e.g., being hold against) the corresponding solid facets of cube 66, using blocks 77A, 77B, 77C and 77D, respectively.

In some embodiments, after fastening the facets of PCB 99, the blocks are fixated to base 90 by inserting respective pins, through the bores of each block and into the respective bores of base 90. For example, pin 79C is inserted through bore 78C of block 77C, and into bore 83C of base 90, for fixating block 90 at the desired position on upper surface 92 of base 90, as described in FIG. 4 above.

At a second folding step 108, facet 88F (also referred to herein as a sixth facet of PCB 99) is folded on solid facet 66F, which is the upper solid facet of cube 66. At a second fastening step 110, facet 88F is fastened to (e.g., being hold against) solid facet 66F, by rotating knob 76 of fastener 72 as described in FIGS. 2 and 4 above, or by using any other suitable technique.

At an edges coupling step 112, PCB 99 is assembled to cube 66 by coupling the edges of adjacent PCB facets to one another. For example, facets 88C and 88D are coupled to one another by coupling between respective edges 97A and 97B, as described in FIG. 3 above. Note that jig 55 is configured to hold PCB 99 in a folded three-dimensional configuration, wrapped around cube 66, so that the aforementioned operator or robot is free to couple the edges of the fastened facets of PCB 99, as described in FIGS. 2-4 above.

At a cube removal step 114 that concludes the method of FIG. 5, TAPS 11 of FIGS. 1 and 2 above (comprising cube 66 wrapped with PCB 99), is removed from jig 11. In some embodiments, the removal of TAPS 11 may be carried out by rotating knob 76 counterclockwise, and by pulling the pins (e.g., pin 79C) and moving the respective blocks (e.g., block 77C) away from assembled TAPS 11.

In some embodiments, after concluding the method of FIG. 5, TAPS 11 may be coupled to cable 54 and inserted to or molded into any suitable housing, which is configured to be attached to the forehead of patient 22, as described in FIG. 1 above.

Although the embodiments described herein mainly address assembling position sensors used in medical applications, the methods and systems described herein can also be used in other applications, such as in assembling any device wrapped with and/or packaged by a foldable substrate.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A jig, comprising:
   a base having an upper surface, which is configured to receive a substrate shaped as a flattened polyhedron having multiple facets; and
   one or more movable blocks, which are configured to move on the base so as to fold respective ones of the multiple facets, and to hold the substrate in a folded three-dimensional configuration.

2. The jig according to claim 1, wherein the base comprises a track for moving one of the one or more movable blocks.

3. The jig according to claim 1, the substrate comprises a foldable section between adjacent facets, and wherein at least one of the one or more movable blocks is configured to fold the foldable section and to fasten one of the adjacent facets to a respective solid facet of a solid polyhedron.

4. The jig according to claim 1, further comprising at least a fixation apparatus, which is configured to fixate at least one of the one or more movable blocks at a predefined position on the base.

5. The jig according to claim 1, further comprising a knob, which is fixated to the base and is configured to fasten at least one of the facets to a respective solid facet of a solid polyhedron.

6. The jig according to claim 5, further comprising a mechanical supporting part, which is configured to be fixated to the base and has a bore, wherein the knob is configured to pass through the bore, such that a distal end of the knob is configured to be moved toward the solid polyhedron for fastening the at least one of the facets to the respective solid facet.

7. The jig according to claim 6, wherein the mechanical supporting part comprises a bridge that goes over the solid polyhedron, and wherein, when the bridge is fixated to the base, the bore is aligned with the respective solid facet.

8. The jig according to claim 6, wherein the knob comprises a screw, and the bore comprises a screw-shaped bore configured to snugly fit over the screw.

9. The jig according to claim 8, wherein the knob is configured to be rotated in first and second directions that are opposite to one another, wherein when the knob is rotated in the first direction, the distal end is configured to move toward the solid polyhedron, and when the knob is rotated in the second direction, the distal end is configured to move away from the solid polyhedron.

10. The jig according to claim 1, wherein the substrate comprises an upper facet, a lower facet and one or more additional facets, wherein a solid polyhedron is positioned on the lower facet, wherein the one or more movable blocks are configured to fasten respective ones of the additional facets to respective solid facets of the solid polyhedron, further comprising a knob, which is configured to fasten the upper facet to an upper solid facet of the solid polyhedron.

11. The jig according to claim 1, the base comprising a first track associated with the upper surface, the one or more movable blocks comprising a first block configured to slide along a first path defined by the first track.

12. The jig according to claim 11, the base comprising a second track associated with the upper surface, the one or more movable blocks comprising a second block configured to slide along a second path defined by the second track.

13. The jig according to claim 12, the first track and the second track extending perpendicular relative to each other.

14. The jig according to claim 12, the first track and the second track extending coaxially relative to each other.

15. The jig according to claim 12, the first track and the second track each defining a respective bore dimensioned to receive a respective pin.

16. The jig according to claim 1, the flattened polyhedron comprising at least six facets.

17. A jig, comprising:
(a) a base having an upper surface, which is configured to receive:
  (i) a substrate shaped as a flattened piece of a flexible printed circuit board (PCB) having multiple facets, and
  (ii) a body comprising a ferrite material; and
(b) one or more movable blocks, which are configured to move on the base so as to fold respective ones of the multiple facets against the body, and to hold the piece of PCB in a folded three-dimensional configuration.

18. The jig of claim 17, the body comprising a cube.

19. The jig of claim 18, the PCB comprising six facets.

20. A jig, comprising:
(a) a base having an upper surface, the upper surface comprising a first track and a second track, the upper surface dimensions to receive:
  (i) a substrate shaped as a flattened piece of substrate having multiple facets, and
  (ii) a body comprising a ferrite material such that a facet of the substrate is interposed between the upper surface and the body;
(b) a first movable block associated with the first track; and
(c) a second movable block associated with the second track, the first movable block and the second movable block are configured to move on the base so as to fold respective ones of the multiple facets against the body, and to hold the substrate in a folded three-dimensional configuration.

* * * * *